(12) United States Patent
Prakash et al.

(10) Patent No.: US 11,411,227 B2
(45) Date of Patent: Aug. 9, 2022

(54) ENERGY GENERATION FROM FABRIC ELECTROCHEMISTRY

(71) Applicant: OHIO STATE INNOVATION FOUNDATION, Columbus, OH (US)

(72) Inventors: Shaurya Prakash, Columbus, OH (US); Vishwanath V. Subramaniam, Columbus, OH (US); Chandan Sen, Columbus, OH (US); Asimina Kiourti, Columbus, OH (US); Shomita Steiner, Olean, NY (US); Piya Das Ghatak, Columbus, OH (US); Ramandeep Vilkhu, Lewis Center, OH (US); Anne Co, Columbus, OH (US); Wesley Joo-Chen Thio, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 141 days.

(21) Appl. No.: 16/490,789

(22) PCT Filed: Mar. 2, 2018

(86) PCT No.: PCT/US2018/020725
§ 371 (c)(1),
(2) Date: Sep. 3, 2019

(87) PCT Pub. No.: WO2018/161005
PCT Pub. Date: Sep. 7, 2018

(65) Prior Publication Data
US 2020/0006783 A1    Jan. 2, 2020

Related U.S. Application Data

(60) Provisional application No. 62/466,562, filed on Mar. 3, 2017.

(51) Int. Cl.
*A61F 13/00*    (2006.01)
*A61L 15/44*    (2006.01)
(Continued)

(52) U.S. Cl.
CPC ............ *H01M 6/045* (2013.01); *A41D 1/005* (2013.01); *A41D 31/12* (2019.02);
(Continued)

(58) Field of Classification Search
CPC ... A41D 1/005; A41D 31/12; A61F 13/00017; A61F 13/00034; A61F 13/00012;
(Continued)

(56) References Cited

U.S. PATENT DOCUMENTS

2005/0004550 A1    1/2005    Sun et al.
2005/0085751 A1    4/2005    Daskal et al.
(Continued)

FOREIGN PATENT DOCUMENTS

GB    2434544 A    8/2007
WO    02098502 A2    12/2002
(Continued)

OTHER PUBLICATIONS

European Extended Search Report issued for Application No. 18760876.5, dated Nov. 12, 2020.
(Continued)

*Primary Examiner* — Eugenia Wang
(74) *Attorney, Agent, or Firm* — Meunier Carlin & Curfman LLC

(57) ABSTRACT

Disclosed and described herein are systems and methods of energy generation from fabric electrochemistry. An electrical cell is created when electrodes (cathodes and anodes) are 'printed' on or otherwise embedded into fabrics to generate DC power when moistened by a conductive bodily liquid such as sweat, wound, fluid, etc. The latter acts, in turn, as
(Continued)

the cell's electrolyte. A singular piece of fabric can be configured into multiple cells by dividing regions of the fabric with hydrophobic barriers and having at least one anode-cathode set in each region. Flexible inter-connections between the cells can be used to scale the generated power, per the application requirements.

24 Claims, 7 Drawing Sheets

(51) Int. Cl.
| | |
|---|---|
| D03D 1/00 | (2006.01) |
| D06M 11/83 | (2006.01) |
| H01M 4/06 | (2006.01) |
| H01M 4/38 | (2006.01) |
| H01M 4/54 | (2006.01) |
| H01M 50/411 | (2021.01) |
| H01M 50/44 | (2021.01) |
| H01M 6/04 | (2006.01) |
| A41D 1/00 | (2018.01) |
| A41D 31/12 | (2019.01) |

(52) U.S. Cl.
CPC .. *A61F 13/00017* (2013.01); *A61F 13/00034* (2013.01); *A61F 13/00063* (2013.01); *A61L 15/44* (2013.01); *D03D 1/0088* (2013.01); *D06M 11/83* (2013.01); *H01M 4/06* (2013.01); *H01M 4/38* (2013.01); *H01M 4/54* (2013.01); *H01M 50/411* (2021.01); *H01M 50/44* (2021.01); *A61F 13/00012* (2013.01); *D10B 2401/16* (2013.01); *D10B 2401/18* (2013.01); *D10B 2403/02431* (2013.01); *H01M 2220/30* (2013.01)

(58) Field of Classification Search
CPC . A61F 13/00063; A61L 15/44; D03D 1/0088; D06M 11/83; D10B 2401/16; D10B 2401/18; D10B 2403/02431; H01M 6/045; H01M 6/46; H01M 6/04; H01M 4/06; H01M 4/38; H01M 4/54; H01M 50/411; H01M 50/44; H01M 2220/30
See application file for complete search history.

(56) References Cited

U.S. PATENT DOCUMENTS

| | | | |
|---|---|---|---|
| 2007/0060862 A1 | 3/2007 | Sun et al. | |
| 2009/0062723 A1 | 3/2009 | Skiba | |
| 2010/0069813 A1* | 3/2010 | Crisp | A61F 13/00021 602/46 |
| 2010/0204752 A1 | 8/2010 | Tremblay et al. | |
| 2011/0015697 A1 | 1/2011 | McAdams | |
| 2011/0112465 A1 | 5/2011 | Anderson et al. | |
| 2011/0271424 A1 | 11/2011 | Revol Cavalier | |
| 2013/0095138 A1 | 4/2013 | Norton et al. | |
| 2015/0126834 A1 | 5/2015 | Wang et al. | |
| 2015/0374984 A1* | 12/2015 | King | A61N 1/328 607/50 |
| 2016/0059009 A1 | 3/2016 | Skiba et al. | |
| 2016/0081580 A1 | 3/2016 | Bergelin et al. | |
| 2017/0229704 A1* | 8/2017 | Takahashi | H01M 10/0569 |
| 2019/0247234 A1 | 8/2019 | Prakash et al. | |

FOREIGN PATENT DOCUMENTS

| | | | |
|---|---|---|---|
| WO | 2007088348 | 12/2007 | |
| WO | 2014188070 | 11/2014 | |
| WO | WO-2016021684 A1 * | 2/2016 | ............ H01M 4/587 |
| WO | 2016044341 | 3/2016 | |
| WO | 2016100307 A1 | 6/2016 | |

OTHER PUBLICATIONS

International Search Report and Written Opinion issued by the International Searching Authority (ISA/US) in PCT Application No. PCT/US2018/020725 dated May 16, 2018. 8 pages.
European Extended Search Report issued for Application No. 17861617, dated May 4, 2020.
Metcalf, D., Milliard, S.T.J., Gomez, M., Schwartz, M.: 'Wearables and the Internet of Things for health: wearable, interconnected devices promise more efficient and comprehensive health care', IEEE Pulse, 2016, 7, (5), pp. 35-39.
Islam, A., Kiourti, A., Volakis, J.L.: 'A novel method of deep tissue biomedical imaging using a wearable sensor', IEEE Sensors J., 2016, 26, (1), pp. 265-270.
Mukhopadhyay, S.C.: 'Wearable sensors for human activity monitoring: a review', IEEE Sensors J., 2015, 15, (3), pp. 1321-1330.
International Data Corporation (IDC), Press Release, Mar. 17, 2016. https://www.idc.com/getdoc.jsp?containerId=prUS41100116.
Jost, K., Dion, G., Gogotsi, Y.: 'Textile energy storage in perspective', J. Mater. Chem., 2014, 28, (2), pp. 10776-10787.
Zheng, Y.-L., Ding, X.-R., Poon, C.C.Y., Lo, B.P.L., Zhang, H., Zhou, X.-L., Yang, G.-Z., Zhao, N., Zhang, Y.-T.: 'Unobtrusive sensing and wearable devices for health informatics', IEEE Trans. Biomed. Eng., 2014, 61, (5), pp. 1538-1554.
Lee, Y.H., Kim, J.S., Noh, J., Lee, I., Kim, H.J., Choi, S., Seo, J., Jeon, S., Kim, T.S., Lee, J.Y., Choi, J.W.: 'Wearable textile battery rechargeable by solar energy', Nano Letters, 2013, 13, (11), pp. 5753-5761.
Olgun, U., Chen, C.C., Volakis, J.L.: 'Investigation of rectenna array configurations for RF power harvesting', IEEE Antennas Wireless Propag. Lett., 2011, 10, pp. 262-265.
Syscom Advanced Materials, Amberstrand fiber. 2015. https://www.metalcladfibers.com/amberstrand/.
H. Elayan, R.M. Shubair, and A. Kiourti, "Wireless sensors for medical applications: Current status and future challenges," in Proc. Europ. Conf. Antennas Propag., Mar. 2017.
He, B., Baird, R., Datta, A., George, S., Hecht, B., et al.: 'Grand challenges in interfacing engineering with life sciences and medicine', IEEE Trans. Biomed. Eng., vol. 60, No. 3, pp. 589-598, 2013.
M.A. Hannan, S. Mutashar, S.A. Samad, and A. Hussain, "Energy harvesting for the implantable biomedical devices: issues and challenges," Biomed. Eng. Online, vol. 13, 2014.
Vomaris: 'Procellera: Wound care with advanced microcurrent technology', http://procellera.com/, accessed Nov. 2016, 6 pages.
Banerjee, J., Das Ghatak, P., Roy, W., Khanna, S., Sequin, E.K., et al.: 'Improvement of human keratinocyte migration by a redox active bioelectric dressing', PLOS One, vol. 9, No. 3, pp. 1-14, 2014.
Bennett, Molly Abstract for "Design, Fabrication, and Characterization of Electroceutical Bandages for Treatment of Chronically Infected Wounds." Electronic Thesis or Dissertation. Ohio State University, Sep. 30, 2016. https://etd.ohiolink.edu/ (This is a publication by one of the inventors that occurred less than one year before the effective filing date of the present application and thus is not prior art to the present application, but is submitted to provide the Examiner with an idea of the state of the art at the time of the invention.)
Costerton, J. W., Stewart, P. S., & Greenberg, E. P. (1999). Bacterial Biofilms: A Common Cause of Persistent Infections. Science, 284(5418), 1318-1322. doi 10.1126/science.284.5418.1318.
Hurlow et al., Clinical Biofilms: A Challenging Frontier in Wound Care. Adv. Wound Care, 2015, 4(5): 295-301.
International Preliminary Report on Patentability issued by the International Bureau of WIPO in PCT Application No. PCT/US2018/020725 dated Sep. 12, 2019. 6 pages.
International Preliminary Report on Patentability issued for Application No. PCT/US2017/057597, dated May 2, 2019, 7 pages.
International Search Report and Written Opinion. Issued by the US International Searching Authority. Application No. PCT/US2017/057597. dated Jan. 5, 2018. 9 pages.
Klasson, David H. "Treatment of Chronic Venous Leg Ulcers With Raw Silk." Angiology 17.6 (1966): 369-376.

(56) References Cited

OTHER PUBLICATIONS

Sandvik, E. L., McLeod, B. R., Parker, A. E., & Stewart, P. S. (2013). Direct electric current treatment under physiologic saline conditions kills *Staphylococcus epidermidis* biofilms via electrolytic generation of hypochlorous acid. PLOS ONE, 8(2), e55118. doi: 10.1371/journal.pone.0055118.
International Search Report and Written Opinion issued for Application No. PCT/US2021/026414, dated Aug. 31, 2021.
Kiamco, Mia Mae, et al. "Hypochlorous-acid-generating electrochemical scaffold for treatment of wound biofilms." Scientific reports 9.1 (2019): 1-13.
Arenschield, I., "Electrifying wound care: Better bandages to destroy bacteria", Retrieved on Jun. 16, 2021 https://news.psu.edu/electrifying-wound-care-better-bandages-to-destroy-bacteria/.
Dusane, Devendra H., et al. "Electroceutical treatment of Pseudomonas aeruginosa biofilms." Scientific reports (2019) 9:2008. Retreived on Jun. 16, 2021. https://www.nature.com/articles/s41598-018-37891-y.

\* cited by examiner

ENERGY GENERATION FROM FABRIC ELECTROCHEMISTRY

CROSS-REFERENCE TO RELATED APPLICATIONS

This application is a national stage application filed under 35 U.S.C. § 371 of PCT/US2018/020725 filed Mar. 2, 2018, which claims priority to and benefit of U.S. provisional patent application No. 62/466,562 filed Mar. 3, 2017, both of which are fully incorporated by reference and made apart hereof.

TECHNICAL FIELD

The present disclosure is generally directed to devices and methods for generating electrical energy using fabric electrochemistry. More specifically, the present disclosure is directed to a fabric that has anodic and cathodic materials printed, woven or otherwise attached to or embedded in the fabric. Moisture serves as an electrolyte causing a reduction-oxidation (redox) reaction between the anode and cathode, thus generating electrical energy that can be harvested for useful purposes. The moisture may come from any conductive liquid, for example, sweat from a person wearing the fabric, wound exudate, saline, water, and the like.

BACKGROUND

Wearable electronics are becoming increasingly popular for consumer, sports, and healthcare applications. For example, the International Data Corporation (IDC) predicts shipment of over 237 million wearable devices (smart watches, bracelets, socks, shirts, etc.) by 2020. One of the biggest challenges associated with wearable devices relates to the way of powering them. Conventional batteries are typically employed, but they are bulky and require frequent recharging and/or replacement. With this in mind, alternate power-generating technologies are recently being explored, which, are, however, associated with several drawbacks. For example, solar energy harvesters occupy large surfaces, require bulky/rigid energy-collecting panels, and only collect energy at certain times of the day. Another popular method, namely Radio-Frequency (RF) power harvesting, requires an RF source within close proximity of the wearer, exhibits low efficiency, and requires bulky/rigid circuitry to perform the AC-to-DC conversion.

Therefore, a need remains to unobtrusively power wearable electronics that overcomes challenges in the art, some of which are described above.

SUMMARY

Disclosed and described herein are systems and methods for energy generation from fabric electrochemistry. An electrical cell is created when electrodes (a cathode and an anode) are 'printed' on or otherwise embedded into fabrics to generate DC power when moistened by a conductive bodily liquid such as sweat, wound exudate, fluids, etc. The latter acts, in turn, as the cell's electrolyte. A singular piece of fabric can be configured into multiple cells by dividing regions of the fabric with hydrophobic barriers and having at least one anode-cathode set in each region. Flexible inter-connections between the cells can be used to scale the generated power, per the application requirements.

One electrochemical fabric comprises one or more cells. Each of the one or more cells are comprised of a fabric substrate and at least one pair of electrodes positioned on or within the fabric substrate. The pair of electrodes comprise an anode and a cathode. Further comprising each of the one or more cells is an electrolyte, wherein the electrolyte causes a reduction-oxidation (redox) reaction between the anode and cathode that generates electrical energy that can be harvested for useful purposes.

The electrolyte comprises moisture. Generally the moisture comprises any conductive liquid including perspiration from a person wearing the electrochemical fabric, wound exudate, saline, water, and the like. In another embodiment, an electrochemically active fabric (or layers of electrochemically active fabric "sandwiched" together) might be pre-soaked with a strong electrolyte and further used to moisten the cells in the form of an underlying electrolyte "cushion".

In one aspect, the electrochemical fabric comprises all or a portion of a garment intended to be worn by a person.

Alternatively or optionally, the electrochemical fabric further comprises circuitry, which may be external or internal to the fabric, connected to the anode and cathode such that the generated electrical energy is used to at least partially power the circuitry. In one aspect, the circuitry may include an energy storage device such as a capacitor, battery, and the like.

Alternatively or optionally, the circuitry may comprise a sensor. For example, the sensor may comprise a wireless sensor. In one aspect, the sensor comprises a batteryless wound sensor.

In some embodiments, the cathode is comprised of oxides of silver ($Ag_2O$) and the anode is comprised of zinc (Zn). In other aspects, at least one of the anode and the cathode are comprised of silver, silver chloride, silver compounds, gold, gold compounds, platinum, platinum compounds, or any other biocompatible electrically-conductive material.

Alternatively or optionally, the electrochemical fabric may comprise a plurality of cells, wherein the plurality of cells are connected using flexible connectors either in electrical series and/or electrical parallel to increase a voltage and/or a current of the generated electrical energy. Generally, each of the plurality of cells is separated from an adjoining cell by a hydrophobic barrier.

Flexible connectors used to inter-connect different cells can be realized using conductive wires or traces. These may be implemented via conductive inks, conductive threads, conductive wires, and the like. These conductive inter-connections might be pre-printed on the fabric, followed by deposition of the anode and cathode materials and the hydrophobic barrier. Alternatively, the anode and cathode materials and the hydrophobic barrier might be printed first, followed by deposition or attachment of the conductive inter-connections.

Generally, the fabric substrate is comprised of material that is substantially electrically insulating when dry such as silk, cotton, polyester, and the like.

At least one of the anode and the cathode can be printed on the fabric substrate using, for example, screen-printing techniques, printed on the fabric substrate using a printer, and the like.

In other aspects, at least one of the anode and the cathode are woven into the fabric substrate.

In one non-limiting example, at least a portion of the electrochemical fabric comprises a Procellera™ Antimicrobial Wound Dressing.

Also disclosed and described herein is a method of electrical energy generation. The method comprises wearing, by a person, a garment, wherein at least a portion of the garment comprises an electrochemical fabric. The electrochemical fabric is comprised of one or more cells, wherein each cell comprises a fabric substrate; and at least one pair of electrodes positioned on or within the fabric substrate, wherein the pair of electrodes comprise an anode and a cathode. The method further comprises generating energy from the electrochemical fabric when an electrolyte causes a reduction-oxidation (redox) reaction between the anode and cathode that generates electrical energy that can be harvested for useful purposes.

The electrolyte comprises moisture and the moisture comprises any conductive liquid including perspiration from a person wearing the electrochemical fabric, wound exudate, saline, water, and the like. In another embodiment, an electrochemically active fabric (or layers of electrochemically active fabric "sandwiched" together) might be pre-soaked with a strong electrolyte and further used to moisten the cells in the form of an underlying electrolyte "cushion".

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Figure 1A:
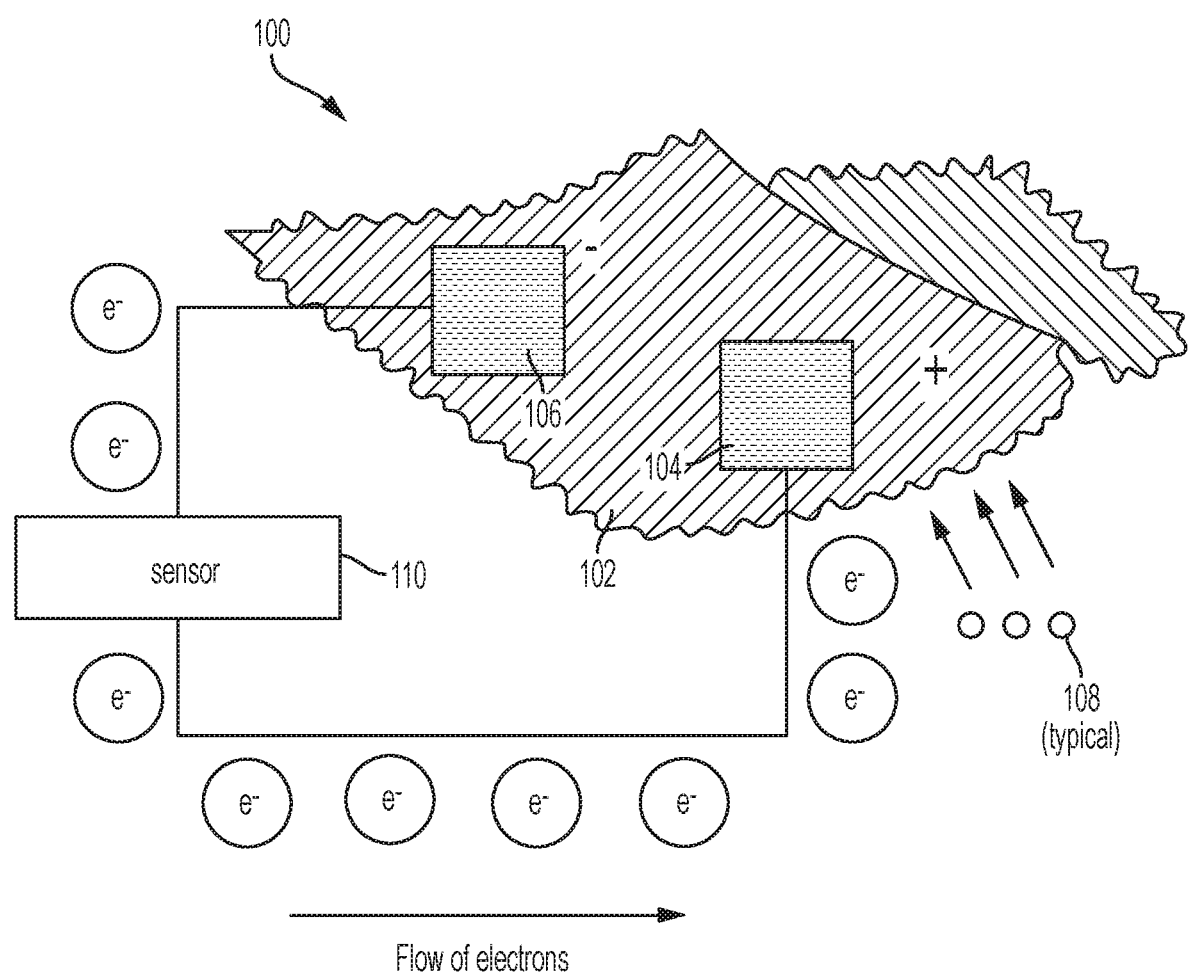
FIG. 1A illustrates an exemplary electrochemical fabric used to form an exemplary battery cell comprised of at least two electrodes on or embedded within a fabric substrate to realize a cathode (positive terminal) and an anode (negative terminal) of the cell.

Disclosed herein are systems and methods of energy generation using fabric electrochemistry. The fabric can be incorporated into or comprise a wearable garment, which can be used to provide power to on-board electronics and/or sensors.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

An exemplary electrochemical fabric and its principles of operation is summarized in FIG. 1A. As shown in FIG. 1A, an exemplary battery cell 100 is comprised of at least two electrodes on or embedded within a fabric substrate 102 to realize a cathode (positive terminal) 104 and an anode (negative terminal) 106 of the cell 100, thereby forming an electrochemical fabric. When the fabric substrate 102 having the electrodes thereon or embedded within comes into contact with a conductive liquid (e.g., sweat, wound exudate, fluids, etc.) 108, the latter acts as an electrolyte, causing the anode 106 to oxidize, and the battery cell 100 to generate DC power when connected to external circuitry 110 such as a sensor (e.g., temperature sensor, accelerometer, gyroscope, humidity sensor, barometric pressure sensor, etc.). For example, in one of the embodiments the electrochemical fabric may comprise oxides of silver ($Ag_2O$) and zinc (Zn) at the cathode 104 and anode 106, respectively. In this particular case, when the cathode 104 interacts with the conductive liquid 108, $OH^-$ ions are generated from the reaction in Eq. (1), below. These $OH^-$ ions then migrate to the anode 106 and are consumed as seen in Eq. (2), below. In this way, DC voltage and current are generated just by getting the electrochemical fabric moistened via a conductive liquid 108.

$$Ag_2O + H_2O + 2e^- \rightarrow 2Ag + 2OH^- \quad (1)$$

$$Zn + 2OH^- \rightarrow ZnO + H_2O + 2e^- \quad (2)$$

In the above example, the electrodes are comprised of silver ($Ag_2O$) and zinc (Zn), though it is to be appreciated that the electrodes can be comprised of any materials that undergo a reduction-oxidation process that generates electrical energy in the presence of an electrolyte. Generally, the anode 106 and the cathode 104 are comprised of biocompatible electrically-conductive materials. Non-limiting examples of other materials that may be used for the electrodes include silver, silver chloride, silver compounds, gold, gold compounds, platinum, platinum compounds, and/or binary alloys of platinum, cobalt or palladium with phosphorus, or binary alloys of platinum, nickel, cobalt or palladium with boron, cadmium, lithium, aluminum, iridium, mixed metal oxides, metal phosphates, metal nanoparticles, and the like. Non-metallic materials are also contemplated for electrode formation such as conductive polymers and the like. Conductive polymers can include, but are not limited to, polyaniline, polythiophene, polypyrrole, polyphenylene, poly(phenylenevinylene), and the like.

Incorporating engineering concepts into the electrochemistry enables the inter-connection of several of the aforementioned cells 100 in order to boost/scale the generated DC power levels. For example, a voltage boost can be achieved by connecting two or more cells 100 in series. Connections between cells can be implemented via flexible conductive inter-connects, such as conductive E-threads and/or conductive inks. As would be expected, in order to achieve the desired voltage scalability, it is desired to enforce a singular anode 106 and cathode 104 per cell. This may be accomplished by electrically interconnecting multiple electrodes on each cell 100 to form a singular cathode 104 and a singular anode 106. Hydrophobic materials may be used to separate individual cells 100 from each other.

Figure 1B:
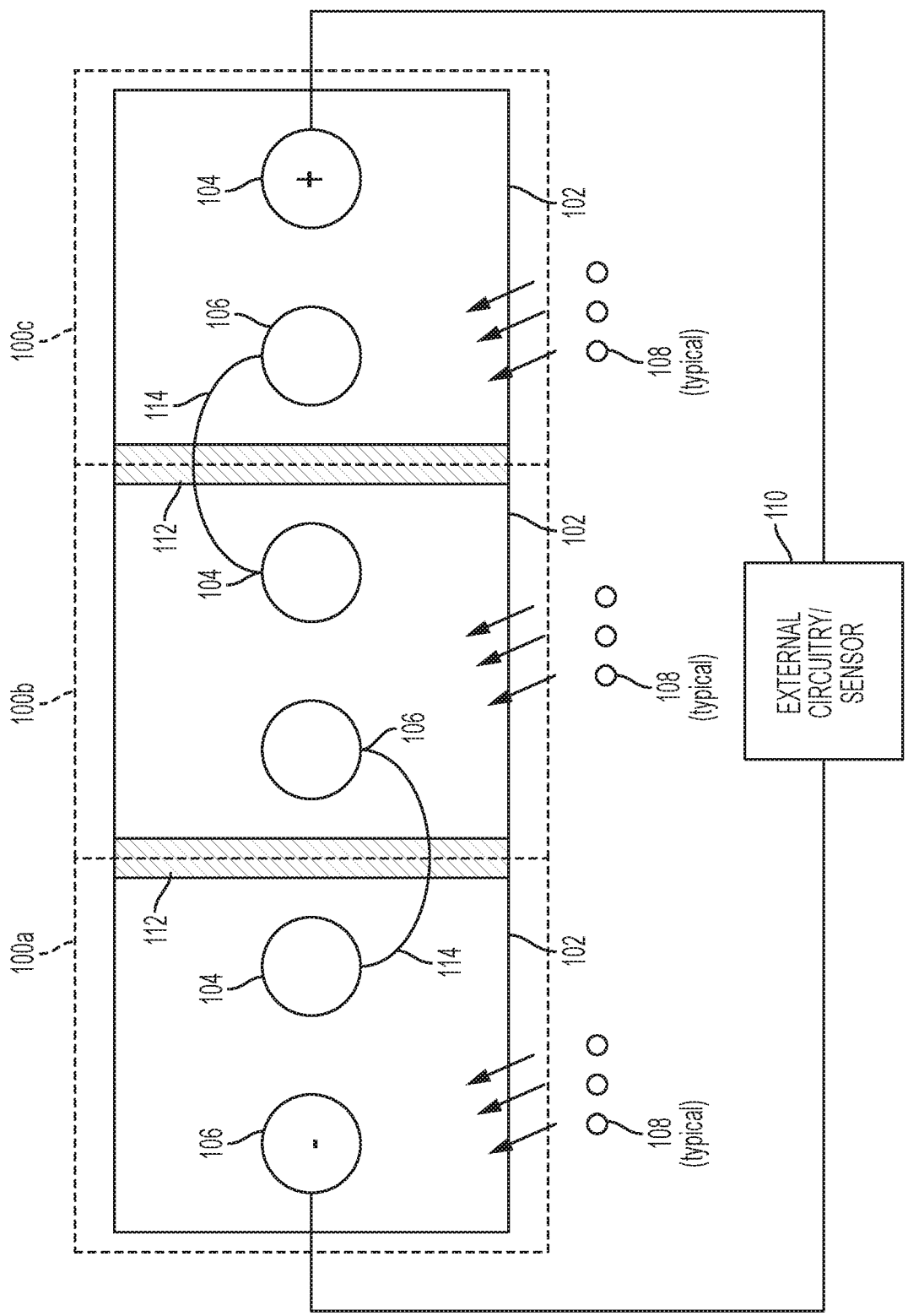
FIG. 1B illustrates an alternate embodiment of an electrochemical fabric used to form a plurality of cells.

FIG. 1B illustrates an alternate embodiment of an electrochemical fabric comprised of a plurality of cells 100a, 100b and 100c. Though FIG. 1B illustrates three cells 100a, 100b, 100c, it is to be appreciated that embodiments of the electrochemical fabric can be comprised of more or fewer cells 100. In the embodiment of FIG. 1B, each of the three cells 100a, 100b and 100c are connected in series so that the voltage supplied to the external circuitry/sensor 110 is additive. Each cell 100a, 100b, 100c is comprised of two electrodes, a cathode 104 and an anode 106, that are printed on, affixed to, or otherwise embedded in a fabric substrate 102. The fabric substrate 102 is generally non-conductive when dry, but made of materials that are generally absorbent or at least wicking (e.g., silk, cotton, hemp, bamboo, cellulose, poly microfiber-based fabrics, etc.). Generally, in regard to the fabric substrate 102, it is comprised of material that is substantially electrically insulating. For example, the fabric substrate 102 may be comprised of silk, cotton, polyester, and the like. In one embodiment of the electrochemical fabric, at least one of the anode 106 or the cathode 104 may be woven into the fabric substrate 102. In one specific example, at least one of the anode 106 or the cathode 104 comprise a conductive silver material woven into the fabric substrate 102.

In other examples, at least one of the anode 106 or the conductive cathode 104 may be printed on the fabric substrate 102 using, for example, conductive printing techniques. For example, at least one of the anode 106 or the cathode 104 may be printed on the fabric substrate 102 using screen-printing techniques, using a (conductive) ink-jet printer, and the like. It is to be appreciated that any other deposition or incorporation methods may be used to form the anode 106 and/or cathode 104 on or within the fabric substrate 102.

The anode 106 and the cathode 104 may be of any size and/or shape and may have varying distances between the anode 106 and the cathode 104. For non-limiting examples, anodes 106 and cathodes 104 may range in size in the 1 mm-10 mm range, with distances between them varying within the 0.2 mm-10 mm range.

When the fabric substrate 102 becomes moist, the moisture acts as an electrolyte to the electrodes, a redox reaction occurs between the cathode 104 and anode 106 of each cell, generating electrical energy. As previously noted, moisture 108 may be derived from perspiration, wound exudate, body fluids including blood, and the like. A flexible conductor 114 electrically connects an anode 106 or cathode 104 of one cell to a cathode 104 or anode 106, respectively, of another cell, so that the cells 100a, 100b, 100c are electrically connected in series. Flexible connectors used to inter-connect different cells can be realized using conductive wires or traces. These may be implemented via conductive inks, conductive threads, conductive wires, and the like. These conductive inter-connections might be pre-printed on the fabric, followed by deposition of the anode and cathode materials and the hydrophobic barrier. Alternatively, the anode and cathode materials and the hydrophobic barrier might be printed first, followed by deposition or attachment of the conductive inter-connections. In some embodiments, a hydrophobic barrier (e.g., hydrophobic sprays, lubricant impregnated surfaces, carbon nanotubes, silicone, etc.) 112 is located between each cell 100a, 100b, 100c to block moisture migration between the cells 100a, 100b, 100c. As noted herein, each cell 100a, 100b, 100c may comprise all or a portion of an article of clothing or garment. Preferably, this article of clothing or garment is at least partially in contact with the skin of a wearer so that perspiration or other exudate from the wearer is transferred to the fabric substrate 102 and/or the electrodes. In some embodiments, an electrochemically active fabric (or layers of electrochemically active fabric "sandwiched" together) might be pre-soaked with a strong electrolyte and further used to moisten the cells in the form of an underlying electrolyte "cushion".

Figure 1C:
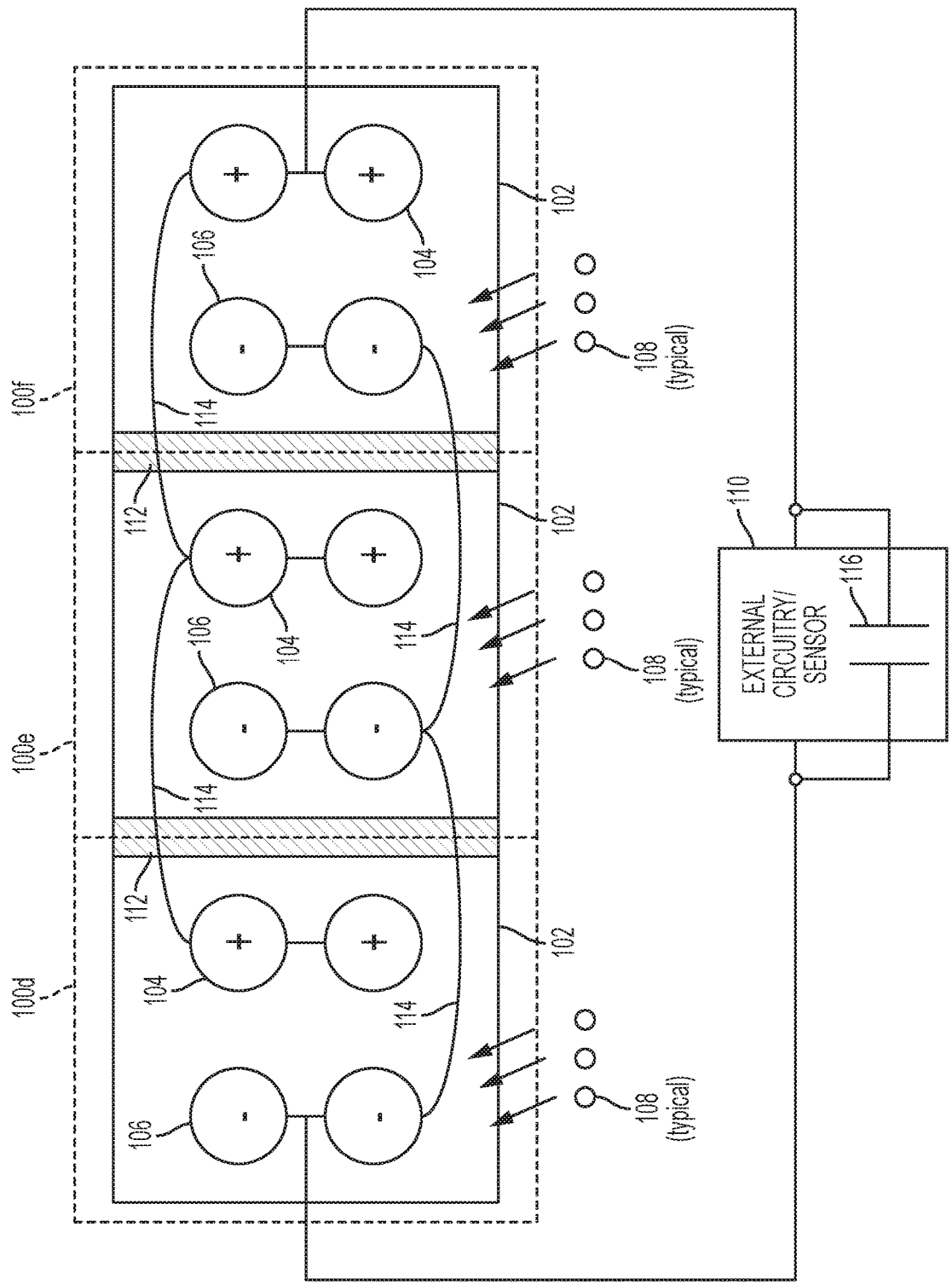
FIG. 1C illustrates yet another alternate embodiment of an electrochemical fabric comprised of a plurality of cells.

FIG. 1C illustrates yet another alternate embodiment of an electrochemical fabric comprised of a plurality of cells 100d, 100e and 100f. Though FIG. 1C illustrates three cells 100d, 100e, 100f, it is to be appreciated that embodiments of the electrochemical fabric can be comprised of more or fewer cells 100. In the embodiment of FIG. 1C, each of the three cells 100d, 100e and 100f are connected in parallel so that the current supplied to the external circuitry/sensor 110 is additive. Also, in FIG. 1C, each cell 100d, 100e and 100f is comprised of a plurality of cathodes 106 connected in series and a plurality of anodes 104 connected in series. As shown in FIG. 1C, there are two cathodes 106 and two anodes 104 connected in series in each cell 100d, 100e, 100f; however, it is to be appreciated that there may be more or fewer cathodes 106 and/or anodes 104 connected in series in other embodiments. Generally, there are the same number of cathodes 106 connected in series as there are anodes 104 in each cell 100d, 100e, 100f, but this is not required. In some embodiments, a cell 100 may be comprised of more or fewer cathodes 106 connected in series than there are anodes 104 connected in series in the cell 100. By increasing the number of cathodes 106 and/or anodes 104 connected in series in each cell 100d, 100e, 100f, the amount of energy generated by each cell 100d, 100e, 100f can be increased. As shown in FIG. 1C, each cell 100d, 100e, 100f is comprised of four electrodes, two cathodes 106 and two anodes 104, that are printed on, affixed to, or otherwise embedded in a fabric substrate 102. The fabric substrate 102 is generally non-conductive when dry, but made of materials that are generally absorbent or at least wicking (e.g., cotton, hemp, bamboo, cellulose, and poly microfiber-based fabrics). When the fabric substrate 102 becomes moist and the moisture acts as an electrolyte to the electrodes, a redox reaction occurs between the cathodes 106 and anodes 104 of each cell, generating electrical energy. As previously noted, moisture 108 may be derived from perspiration, wound exudate, and the like. A flexible conductor 114 electrically connects the anodes 104 connected in series in a particular cell or the cathodes 106 connected in series in a particular cell to the anodes 104 connected in series or the cathodes 106 connected in series, respectively, of another cell, so that the cells 100d, 100e, 100f are electrically connected in parallel. In some embodiments, a hydrophobic barrier (e.g., hydrophobic sprays, lubricant impregnated surfaces, carbon nanotubes, silicone, etc.) 112 is located between each cell 100d, 100e, 100f to block moisture migration between the cells 100a, 100b, 100c. As noted herein, each cell 100d, 100e, 100f may comprise all or a portion of an article of clothing or garment. Preferably, this article of clothing or garment is at least partially in contact with the skin of a wearer so that perspiration or other exudate from the wearer is transferred to the fabric substrate 102 and/or the electrodes.

Figures 2A, 2B, 2C:
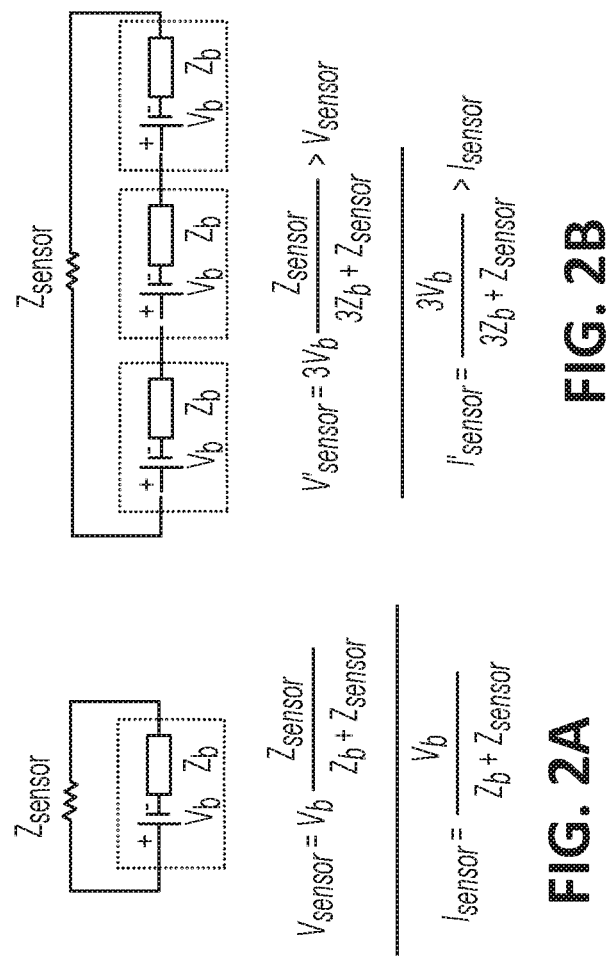
FIGS. 2A, 2B and 2C illustrate equivalent circuit models of the embodiments of electrochemical fabrics of FIGS. 1A, 1B and 1C, respectively.

Equivalent circuit models of the embodiments of electrochemical fabrics of FIGS. 1A, 1B and 1C are shown in FIGS. 2A, 2B and 2C, respectively. In each of FIGS. 2A, 2B and 2C, the electrochemical fabrics are connected in series with external circuitry 110 such as a wearable sensor (impedance of $Z_{sensor}$) are shown in FIGS. 2A, 2B and 2C. Herewith, each battery cell 100 is modeled as a voltage source ($V_b$) with an internal impedance of $Z_b$. These parameters depend on the—per case—electrode materials and patterning. In one non-limiting example, $Z_b$ was measured to be as high as 1.2 MΩ. Basic circuit mathematics for calculating the voltage and current provided to the sensor for each cell configuration of FIGS. 1A, 1B and 1C are shown below the equivalent circuits in FIGS. 2A, 2B and 2C.

As expected, the equations shown in FIGS. 2B and 2C demonstrate the anticipated voltage boost when two or more cells are connected in series and the anticipated current increase when two or more cells are connected in parallel. Of course, more sophisticated configurations may be implemented to scale the output voltage and/or current per the application requirements.

Circuitry 110 may in some embodiments include an energy storage device such as a capacitor (connected in series and/or parallel to a load) 116, a battery, and the like.

EXAMPLES

The present invention has multiple aspects, illustrated by the following non-limiting examples.

In one example, the electrochemical fabric comprises a modified electroceutical dressing such as Procellera™ Antimicrobial Wound Dressing as available from Vomaris Wounds Care, Inc. (Arizona). The Procellera™ Antimicrobial Wound Dressing is comprised of alternating dots of silver and zinc on a bandage substrate. Though intended for expediting wound healing, and not optimized in any way for power generating applications, the Procellera™ dressing still can serve the purposes of a proof-of-principle demonstration. In one example, a 1"×1" Procellera™ dressing was employed in a study. The dressing was moistened in salt water (100 mL water and 5 mL salt).

Figure 3A:
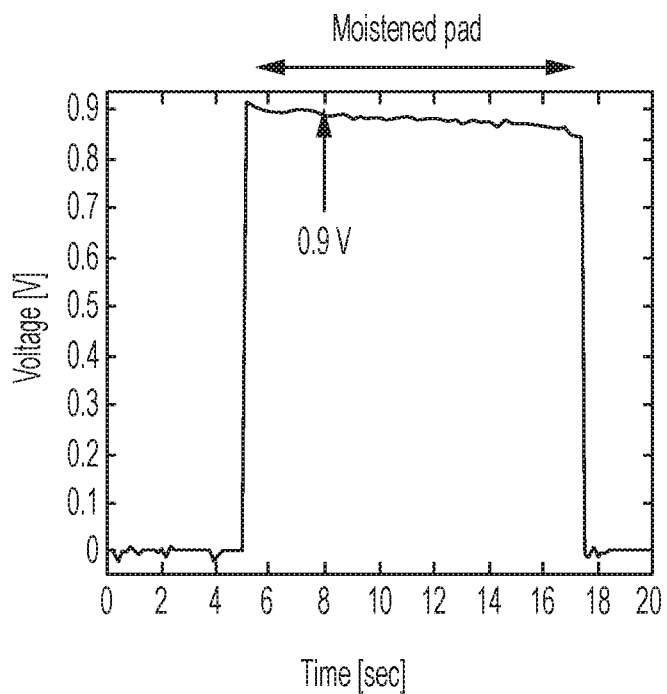
FIG. 3A illustrates exemplary voltage measurements recorded when the positive (silver) and negative (zinc) dots of a moistened Procellera™ dressing were connected to a voltmeter.
Figure 3B:
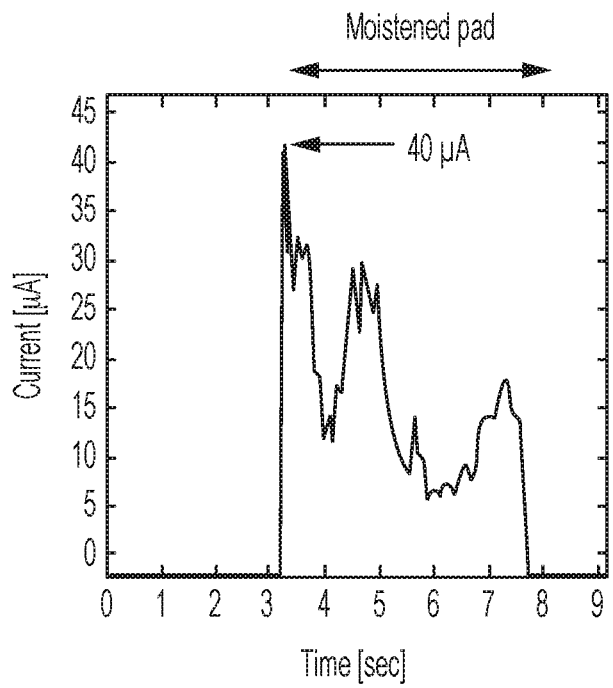
FIG. 3B illustrates a peak current of ~40 μA that was observed when the moistened Procellera™ dressing was connected in series to a current meter.

Voltage measurements recorded when the positive (silver) and negative (zinc) dots of the moistened pad were connected to a voltmeter are shown in FIG. 3A. The observed DC voltage measured from the Procellera™ electrochemical dressing was approximately 0.9V. A peak current of ~40 µA, as shown in FIG. 3B, was observed when the moistened pad was connected in series to a current meter. Remarkably, even these voltage/current levels measured from a proof-of-concept pad are high enough to produce several microwatts of power, enough to power a wide range of low-power electronic sensors.

Figure 3C:
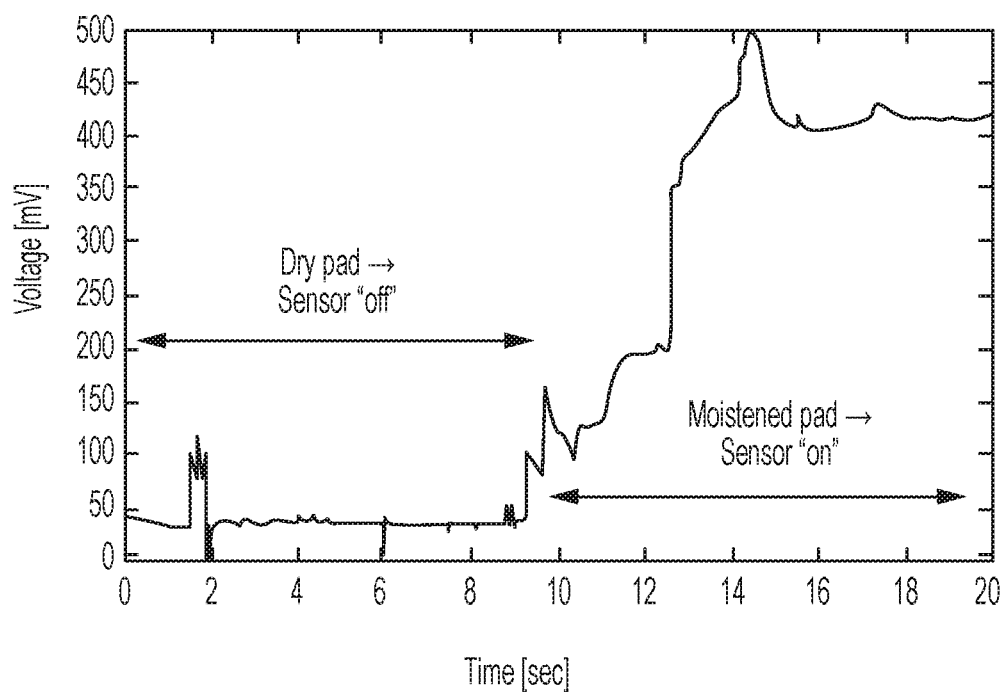
FIG. 3C illustrates an exemplary batteryless wound sensor comprising an electrochemical fabric that generated a detectable voltage across diode terminals when the electrochemical fabric came in contact with a saline solution.

A. Proof-of-Concept Demonstration of Epidermal 'Wound Sensor' Powered via Fabric Electrochemistry A batteryless 'wound sensor' was subsequently demonstrated that was powered via fabric electrochemistry to detect the presence of an underlying open wound. For this particular 'wound sensor', the electrochemical fabric was used to actively monitor the skin surface. In case an underlying wound opens, the resulting exudate acts as an electrolyte for the electrochemical fabric, causing it to generate static voltage. In turn, this voltage is used to activate an indicator/alarm unit and/or wirelessly transmit this information to a remote monitoring/control device. For this proof-of-concept experiment, a diode was used in place of the alarm unit, and a saline solution (100 ml water and 5 ml salt) was use to emulate the wound exudate. When the electrochemical dressing came in contact with the saline solution, a voltage was detected across the diode terminals; therefore, this voltage represented an open wound state (see FIG. 3C). Such a system comprised of electrochemical fabric used in garments could be used to detect wounds in military, police, and other such applications.

Figure 4A:
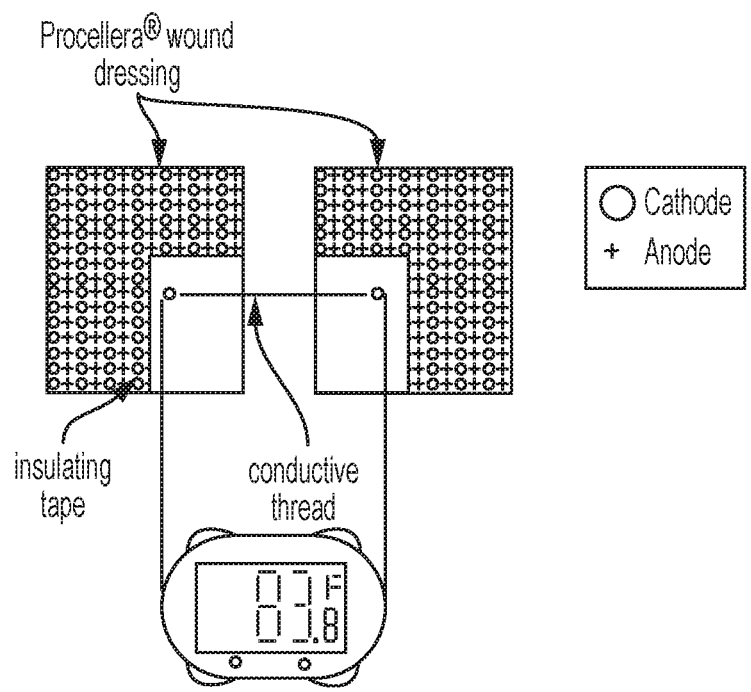
FIG. 4A illustrates another proof-of-concept results where a digital thermometer's display was shown to turn 'on' (flickering) when attached to a series connection of two silver/zinc-based 'printed' battery cells moistened by a saline solution.

FIG. 4A illustrates yet another proof-of-concept results where the feasibility of engineering fully-flexible electrochemical fabrics with power generation capabilities is demonstrated. As shown in FIG. 4A, this proof-of-concept experiment employed two Procellera™ dressings that were moistened via a saline solution (100 mL water and 5 mL salt). Procellera™ dressings are comprised of alternating dots of $Ag_2O$ and Zn, and have recently appeared on the market for wound healing applications. Current Procellera™ dressings have been optimized to initiate cell migration and re-epithelialization in a uniform manner underneath their surface, and they are not engineered in any way for power generating applications. To serve the purposes desired for proof-of-concepts, individual $Ag_2O$ and Zn dot pairs, which correlated to the cells 100 described herein, were electrically isolated from each other using insulating tape adhered to each of the two dressings. Series electrical connections between the two cells 100 was achieved via conductive Amberstrand™ threads (Syscom Advanced Materials, Amberstrand fiber. https://www.metalcladfibers.com/amberstrand/). These threads were comprised of 332 silver-coated polymer filaments that were twisted into a single thread having an overall diameter of ~0.5 mm and a DC resistance of ~0.5 Ω/ft.

Referring to FIG. 4A, a digital thermometer's display was shown to turn 'on' (flickering) when attached to a series connection of two silver/zinc-based 'printed' battery cells moistened by a saline solution (see FIG. 4A). Flickering, as opposed to full operation of the device, was attributed to the employed set-up's current generation capabilities. In fact, the current flowing across the sensor was measured to be 0.4 µA as opposed to the 5.3 µA required to fully operate the thermometer. This flickering is attributed to the low current generation capabilities and the high input impedance of the employed Procellera™ battery cells.

Figure 4B:
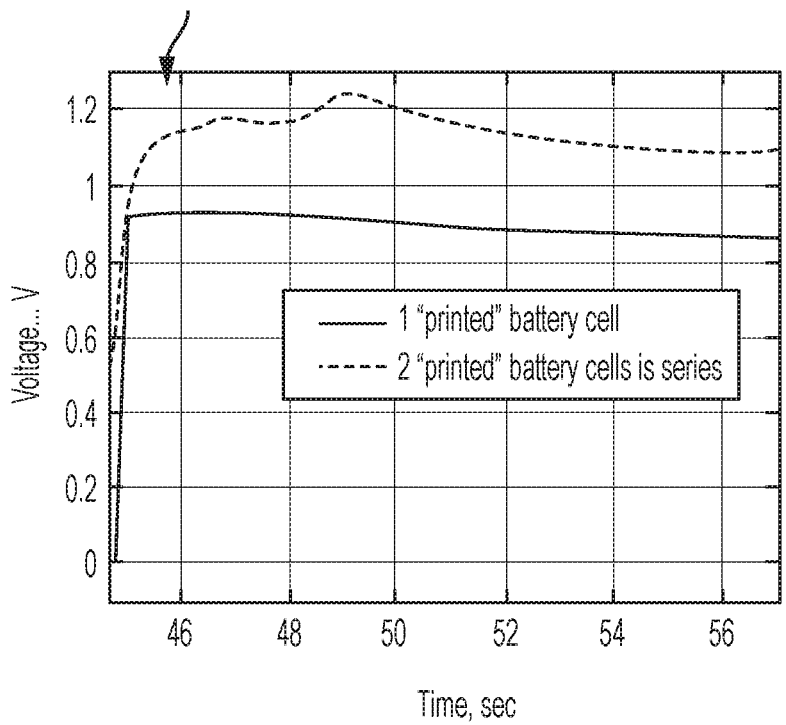
FIG. 4B illustrates a proof-of-concept experiment where a voltage boost is achieved by connecting two cells comprised of Procellera™ dressings in series.

FIG. 4B demonstrates how a voltage boost can be achieved by connecting two Procellera™ cells in series. As illustrated, ~0.9 V generated via a single cell was boosted to ~1.2 V when two cells were connected in series. The reason why the voltage was not linearly boosted (doubled in this case) is due to the high impedance of the Procellera™ cell (1.2 MΩ), which was comparable to the internal impedance of the voltmeter. The steady-state open current flowing through an ammeter connected in series to the Procellera™ dressing was in the range of ~10-11 µA.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain and to illustrate improvements over the present state of the art in claimed invention.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not target to be exhaustive or to limit the embodiments to the precise forms disclosed.

It will be apparent to one of ordinary skill in the art that many modifications and variations are possible in view of the above teachings.

What is claimed is:

1. An electrochemical fabric comprising:
a plurality of cells, wherein each cell comprises:
a fabric substrate;
an anode, wherein the anode is comprised of two or more vertically stacked electrically conductive electrodes, each of the two or more vertically stacked electrically conductive electrodes electrically connected to one another;
a cathode, wherein the cathode is comprised of two or more vertically stacked electrically conductive electrodes, each of the two or more vertically stacked electrically conductive electrodes electrically connected to one another, wherein the two or more electrically conductive electrodes of the cathode and the two or more electrically conductive electrodes of the anode are each spaced apart from any adjoining electrode by a distance of between 0.2 mm and 10 mm;
wherein the two or more of electrically conductive electrodes of the anode and the two or more electrically conductive electrodes of the cathode are positioned on or within the fabric substrate,
wherein two or more electrically conductive electrodes of the cathode and the two or more electrically conductive electrodes of the anode each have a solid circular shape; and
a hydrophobic barrier, wherein the hydrophobic barrier separates each of the plurality of cells from an adjoining cell;
wherein when a liquid electrolyte moistens the fabric substrate of any cell of the plurality of cells the liquid electrolyte causes a reduction-oxidation (redox) reaction between the anode and the cathode of that cell of the plurality of cells that generates electrical energy,
wherein each of the plurality of cells are electrically connected to one another to increase a voltage and/or current of the generated electrical energy.

2. The electrochemical fabric of claim 1, wherein the moisture liquid electrolyte comprises perspiration from a person wearing the electrochemical fabric, wound exudate, saline, blood, body fluids, or water.

3. The electrochemical fabric of claim 1, wherein the electrochemical fabric comprises all or a portion of a garment intended to be worn by a person.

4. The electrochemical fabric of claim 1, further comprising circuitry connected to at least one of the one or more cells such that the generated electrical energy is used to at least partially power the circuitry.

5. The electrochemical fabric of claim 4, wherein the circuitry includes an energy storage device.

6. The electrochemical fabric of claim 5, wherein the energy storage device comprises a capacitor or a battery.

7. The electrochemical fabric of claim 4, wherein the circuitry comprises a sensor.

8. The electrochemical fabric of claim 7, wherein the sensor comprises a wireless sensor.

9. The electrochemical fabric of claim 7, wherein the electrolyte is blood or wound exudate and the sensor comprises a batteryless wound sensor.

10. The electrochemical fabric of claim 1, wherein for each cell of the plurality of cells, the two or more electrically conductive electrodes of the cathode are comprised of oxides of silver ($Ag_2O$) and the two or more electrically conductive electrodes of the anode are comprised of zinc (Zn).

11. The electrochemical fabric of claim 1, wherein the plurality of cells are electrically connected in electrical series to increase a voltage produced by the electrochemical fabric.

12. The electrochemical fabric of claim 1, wherein the hydrophobic barrier comprises one or more of hydrophobic sprays, lubricant impregnated surfaces, carbon nanotubes, and silicone.

13. The electrochemical fabric of claim 1, wherein the plurality of cells are electrically connected in electrical parallel to increase a current produced by the electrochemical fabric.

14. The electrochemical fabric of claim 1, wherein the fabric substrate is comprised of one or more of silk, cotton, polyester, hemp, bamboo, cellulose, and poly microfiber-based fabrics.

15. The electrochemical fabric of claim 1, wherein at least one of the two or more electrically conductive electrodes of the cathode and at least one of the two or more electrically conductive electrodes of the anode of each cell are comprised of silver, silver chloride, silver compounds, gold, gold compounds, platinum, platinum compounds, or any other biocompatible electrically-conductive material.

16. The electrochemical fabric of claim 1, wherein at least one of the two or more electrically conductive electrodes of the cathode and at least one of the two or more electrically conductive electrodes of the anode of each cell are printed on the fabric substrate.

17. The electrochemical fabric of claim 16, wherein the at least one of the two or more electrically conductive electrodes of the cathode and the at least one of the two or more electrically conductive electrodes of the anode of each cell are printed on the fabric substrate using screen-printing techniques or are printed on the fabric substrate using a printer.

18. The electrochemical fabric of claim 1, wherein at least one of the two or more electrically conductive electrodes of the cathode and at least one of the two or more electrically conductive electrodes of the anode of each cell are woven into the fabric substrate.

19. The electrochemical fabric of claim 1, wherein at least a portion of the electrochemical fabric comprises a available modified electroceutical antimicrobial wound dressing.

20. The electrochemical fabric of claim 1, wherein the two or more electrically conductive electrodes of the cathode and the two or more electrically conductive electrodes of the anode each have a solid circular shape having a diameter of between 1 mm and 10 mm.

21. A method of electrical energy generation comprising:
wearing, by a person, a garment, wherein at least a portion of the garment comprises an electrochemical fabric, said electrochemical fabric comprising:
a plurality of cells, wherein each cell comprises:
a fabric substrate;
an anode, wherein the anode is comprised of two or more vertically stacked electrically conductive electrodes, each of the two or more vertically stacked electrically conductive electrodes electrically connected to one another;
a cathode, wherein the cathode is comprised of two or more vertically stacked electrically conductive electrodes, each of the two or more vertically stacked electrically conductive electrodes electrically connected to one another, wherein the two or more electrically conductive electrodes of the cathode and the two or more electrically conductive electrodes of the anode are each spaced apart from any adjoining electrode by a distance of between 0.2 mm and 10 mm;
wherein the two or more electrically conductive electrodes of the anode and the two or more electrically conductive electrodes of the cathode are positioned on or within the fabric substrate,
wherein two or more electrically conductive electrodes of the cathode and the two or more electrically conductive electrodes of the anode each have a solid circular shape; and
a hydrophobic barrier, wherein the hydrophobic barrier separates each of the plurality of cells from an adjoining cell;
moistening at least a portion of the garment with a liquid electrolyte that moistens the fabric substrate of any cell of the plurality of cells causing a reduction-oxidation (redox) reaction between the anode and the cathode of that cell of the plurality of cells that generates electrical energy,
wherein each of the two or more pairs of electrodes plurality of cells are electrically connected to one another to increase a voltage and/or current of the generated electrical energy; and
harvesting the generated electrical energy from the electrochemical fabric when the electrolyte causes the reduction-oxidation (redox) reaction between at least one of the anode and cathode pairs of one of the cells of the plurality of cells that generates electrical energy.

22. The method of claim 21, wherein the liquid electrolyte comprises perspiration from a person wearing the electrochemical fabric, wound exudate, saline, blood, body fluids, or water.

23. The method of claim 21, wherein the electrochemical fabric comprises all or a portion of the garment intended to be worn by a person.

24. The method of claim 21, wherein the two or more electrically conductive electrodes of the cathode and the two or more electrically conductive electrodes of the anode each have a solid circular shape having a diameter of between 1 mm and 10 mm.

* * * * *

UNITED STATES PATENT AND TRADEMARK OFFICE
CERTIFICATE OF CORRECTION

PATENT NO. : 11,411,227 B2
APPLICATION NO. : 16/490789
DATED : August 9, 2022
INVENTOR(S) : Shaurya Prakash et al.

It is certified that error appears in the above-identified patent and that said Letters Patent is hereby corrected as shown below:

In the Claims

In Claim 2, Line 44, delete "moisture".

In Claim 19, Line 45, delete "available".

In Claim 22, Line 34, delete "two or more pairs of electrodes".

Signed and Sealed this
Twenty-fifth Day of October, 2022

Katherine Kelly Vidal
*Director of the United States Patent and Trademark Office*